(12) United States Patent
Mujwid

(10) Patent No.: US 7,297,162 B2
(45) Date of Patent: Nov. 20, 2007

(54) EXPANDABLE HELICAL CAGE

(75) Inventor: James R. Mujwid, Crystal, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 16 days.

(21) Appl. No.: 10/865,673

(22) Filed: Jun. 9, 2004

(65) Prior Publication Data

US 2005/0278028 A1    Dec. 15, 2005

(51) Int. Cl.
*A61F 2/44* (2006.01)

(52) U.S. Cl. ............................................... 623/17.13

(58) Field of Classification Search .. 623/17.11–17.16; 606/53, 60–61, 72–73; 267/162, 166, 168, 267/289–90
See application file for complete search history.

(56) References Cited

U.S. PATENT DOCUMENTS

| | | | | |
|---|---|---|---|---|
| 1,472,782 A | * | 11/1923 | Barber | 464/58 |
| 1,621,428 A | * | 3/1927 | Pedersen et al. | 464/58 |
| 1,923,435 A | * | 8/1933 | Gilpin | 105/15 |
| 2,708,110 A | * | 5/1955 | Clay | 267/162 |
| 4,118,020 A | * | 10/1978 | Myers | 267/168 |
| 4,932,975 A | * | 6/1990 | Main et al. | 623/17.12 |
| 5,055,104 A | * | 10/1991 | Ray | 606/61 |
| 5,368,283 A | * | 11/1994 | Pavlin | 267/155 |
| 5,390,683 A | * | 2/1995 | Pisharodi | 128/898 |
| 5,423,816 A | * | 6/1995 | Lin | 606/61 |
| 5,423,817 A | | 6/1995 | Lin | |
| 5,980,522 A | * | 11/1999 | Koros et al. | 606/61 |
| 6,129,763 A | * | 10/2000 | Chauvin et al. | 623/17.11 |
| 6,174,334 B1 | | 1/2001 | Suddaby | |
| 6,342,076 B1 | * | 1/2002 | Lundborg | 623/21.15 |
| 6,419,705 B1 | * | 7/2002 | Erickson | 623/17.16 |
| 6,436,139 B1 | * | 8/2002 | Shapiro et al. | 623/17.11 |
| 6,436,140 B1 | * | 8/2002 | Liu et al. | 623/17.11 |
| 6,436,142 B1 | * | 8/2002 | Paes et al. | 623/17.15 |
| 6,443,989 B1 | * | 9/2002 | Jackson | 623/17.15 |
| 6,451,057 B1 | * | 9/2002 | Chen et al. | 623/17.15 |
| 6,454,806 B1 | * | 9/2002 | Cohen et al. | 623/17.15 |
| 6,454,807 B1 | * | 9/2002 | Jackson | 623/17.15 |
| 6,500,205 B1 | * | 12/2002 | Michelson | 623/17.16 |
| 6,558,423 B1 | * | 5/2003 | Michelson | 623/17.11 |
| 6,685,742 B1 | * | 2/2004 | Jackson | 623/17.11 |
| 6,773,460 B2 | * | 8/2004 | Jackson | 623/17.15 |
| 6,821,298 B1 | * | 11/2004 | Jackson | 623/17.15 |
| 6,849,093 B2 | * | 2/2005 | Michelson | 623/17.15 |
| 2001/0051829 A1 | | 12/2001 | Middleton | |
| 2002/0068977 A1 | * | 6/2002 | Jackson | 623/17.15 |
| 2002/0128716 A1 | | 9/2002 | Cohen et al. | |
| 2002/0143401 A1 | * | 10/2002 | Michelson | 623/17.16 |
| 2002/0161444 A1 | * | 10/2002 | Choi | 623/17.11 |
| 2003/0149482 A1 | | 8/2003 | Michelson | |
| 2004/0119216 A1 | * | 6/2004 | Menzel et al. | 267/166 |

* cited by examiner

*Primary Examiner*—Eduardo C. Robert
*Assistant Examiner*—Annette Reimers
(74) *Attorney, Agent, or Firm*—Wood, Herron & Evans, LLP

(57) ABSTRACT

An expandable implant having a helical body and first and second securing pieces. Ends of the helical body are connected to the first and second end pieces. The first and second end pieces can be rotated relative to one another to expand the implant from a first dimension to a selected second dimension. The implant further includes a locking arrangement to maintain the implant at the selected second dimension.

19 Claims, 5 Drawing Sheets

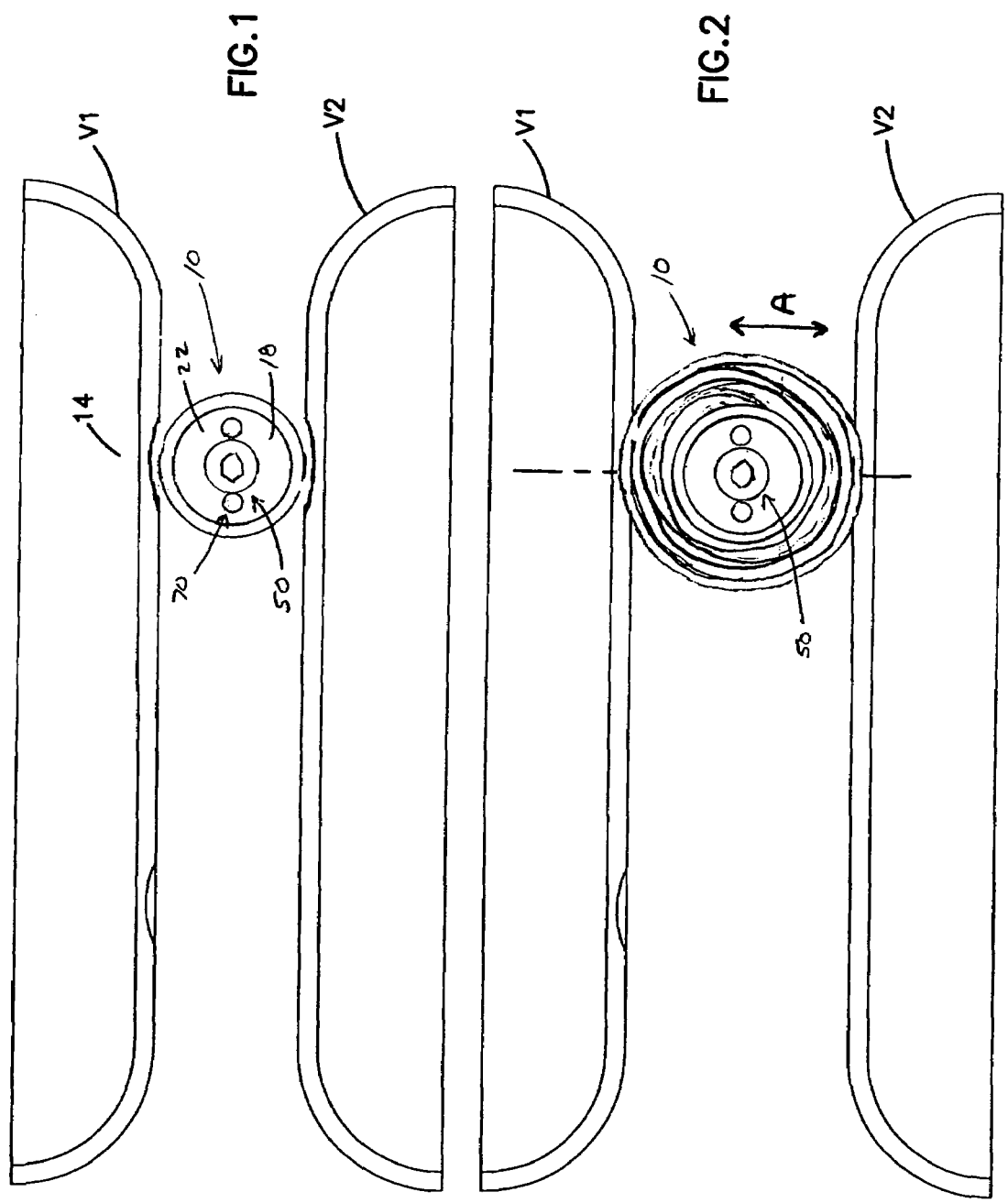

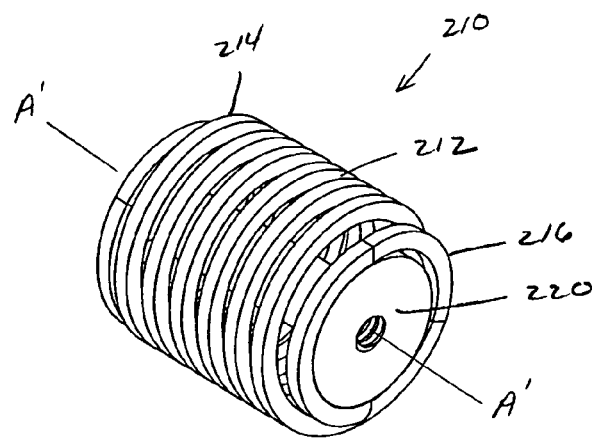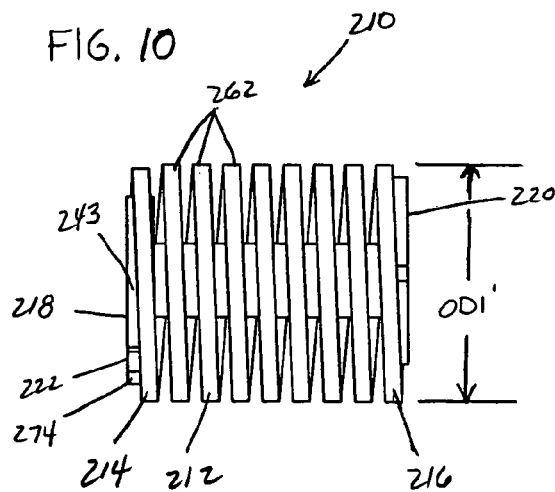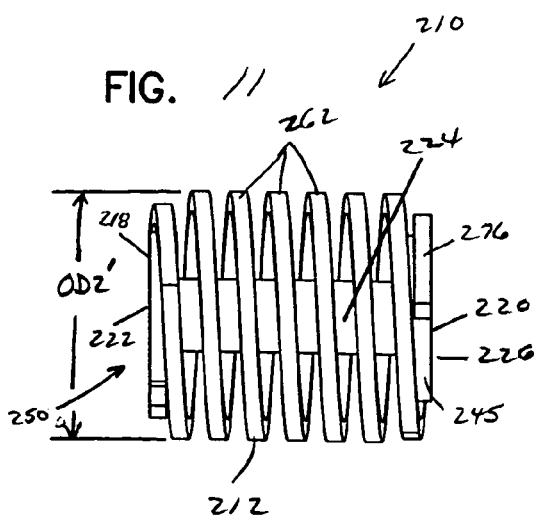

EXPANDABLE HELICAL CAGE

TECHNICAL FIELD

This disclosure relates generally to methods and devices for stabilizing adjacent vertebral elements. More particularly, this disclosure relates to an expandable intervertebral implant.

BACKGROUND

A wide variety of configurations of intervertebral implants have been utilized for stabilizing adjacent vertebral elements and facilitating the development of bone union between the vertebral elements. In some configurations, the intervertebral implants are not adjustable by the surgeon during the surgical procedure. Therefore, the surgeon must choose the size that most closely matches the desired dimensions. Because these implants are of a pre-determined size and shape, the implant site must correspond to the implant configuration. This can require extensive site preparation to complete implantation. Extensive site preparation can compromise the success of the implantation procedure by causing excessive damage to the receiving vertebral elements. In addition, procedures requiring extensive site preparation can result in relatively long surgeries that may increase patient risk.

To address this problem, more recent intervertebral implants have been designed to expand from a first height to a second height. One such intervertebral implant is described in U.S. Pat. No. 6,174,334. This implant includes a pair of shells that when assembled form an implant assembly. Teeth are formed on each shell so that the shells can be uni-directionally spaced apart.

In general, improvement has been sought with respect to implantation procedures and devices, generally to provide an expandable implant assembly that reduces the invasiveness of the procedure and to provide an expandable implant that is easily adjusted during an implantation procedure.

SUMMARY

One aspect of the present invention relates to an expandable intervertebral implant having a helical body and first and second securing pieces. The helical body has a first end and a second end, the first end of the helical body being connected to the first securing piece and the second end of the helical body being connected to the second securing piece. The implant further includes a locking arrangement configured to selectively lock the second securing piece in a rotational orientation relative to the first securing piece.

Another aspect of the present invention relates to a method of expanding an expandable intervertebral implant. The method includes providing an implant having a helical body connected to a first end cap and a second end cap, and inserting the implant at an implant site. The implant is expanded by rotating the first end cap relative to the second end cap such that the helical body radially expands from a first configuration to a second configuration. The implant can be locked in the second configuration.

A variety of examples of desirable product features or methods are set forth in part in the description that follows, and in part will be apparent from the description, or may be learned by practicing various aspects of the disclosure. The aspects of the disclosure may relate to individual features as well as combinations of features. It is to be understood that both the foregoing general description and the following detailed description are explanatory only, and are not restrictive of the claimed invention.

BRIEF DESCRIPTION OF THE DRAWINGS

FIG. 1 is a front elevational view of one embodiment of an expandable intervertebral implant, according to the principles of the present disclosure, shown in a non-expanded position;

FIG. 2 is a front elevational view of the implant of FIG. 1, shown in an expanded position;

FIG. 9 is a perspective view of another embodiment of an expandable intervertebral implant, according to the principles of the present disclosure;

FIG. 10 is a side elevational view of the implant of FIG. 9, shown in a non-expanded position; and FIG. 11 is a side elevational view of the implant of FIG. 10, shown in an expanded position.

DETAILED DESCRIPTION

Reference will now be made in detail to exemplary aspects of the present disclosure that are illustrated in the accompanying drawings. Wherever possible, the same reference numbers will be used throughout the drawings to refer to the same or like parts.

Referring to FIGS. 1 and 2, one embodiment of an expandable intervertebral implant 10 is shown, according to the principles of the present disclosure. The implant 10 in FIG. 1 is shown inserted between two vertebral elements V1, V2 in a relaxed or non-expanded configuration. In FIG. 2, the implant 10 is shown in an expanded configuration.

Figure 3:
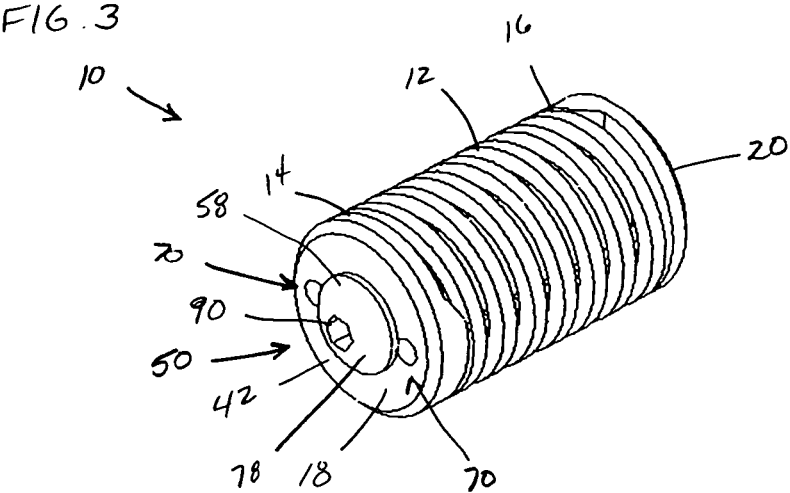
FIG. 3 is front perspective view of the implant of FIG. 1.
Figure 4:
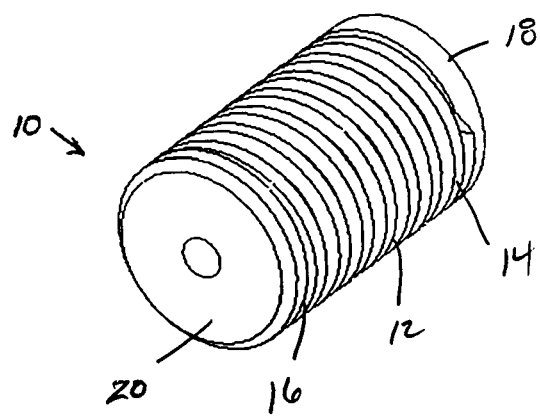
FIG. 4 is a rear perspective view of the implant of FIG. 3.

Referring now to FIGS. 3 and 4, the implant 10 generally includes a helical body 12 having a first end 14 and a second end 16. The first end 14 of the helical body 12 is attached to a first securing piece 18, and the second end 16 is attached to a second securing piece 20.

As shown in FIGS. 1 and 2, the intervertebral implant 10 is configured to expand from a first dimension to a selected second dimension. The implant 10 includes a locking arrangement 50 that secures the implant at the selected second dimension. That is, the implant 10 is configured to permit expansion to, and be secured at, a selected one of a variety of second dimensions. Expansion is accomplished by rotating one end 14, 16 of the helical body 12 in relation to the other end 14, 16. As will be described hereinafter, the implant is also configured to permit contraction from the selected second dimension to a reduced dimension between the second dimension and the first dimension, or contraction back to the first dimension.

Referring again to FIG. 3, the helical body 12 of the implant 10 is typically machined to provide the features herein disclosed. In one embodiment, the helical body is made of titanium, or other biocompatible materials such as stainless steel, graphite, carbon fiber materials, PEEK, nitinol, or various plastics and composites of the foregoing.

Preferably, the helical body material provides the strength necessary to withstand forces from the intervertebral implant when positioned between two vertebral elements. In addition, the material preferably provides the flexibility to change shape or the dimension of the implant 10 by twisting or rotation, as will be described in greater detail hereinafter.

The first and second securing pieces 18, 20 can also be machined, or may be molded to provide the features herein disclosed. Each of the pieces 18, 20 may be made of the same material as the helical body 12, or may be made of a different material than the helical body or one another. Representative materials typically include biocompatible materials such as stainless steel, graphite, carbon fiber materials, PEEK, nitinol, or various plastics and composites of the foregoing. In the preferred embodiment, the first and second securing pieces 18, 20 are made of titanium.

Figure 7:
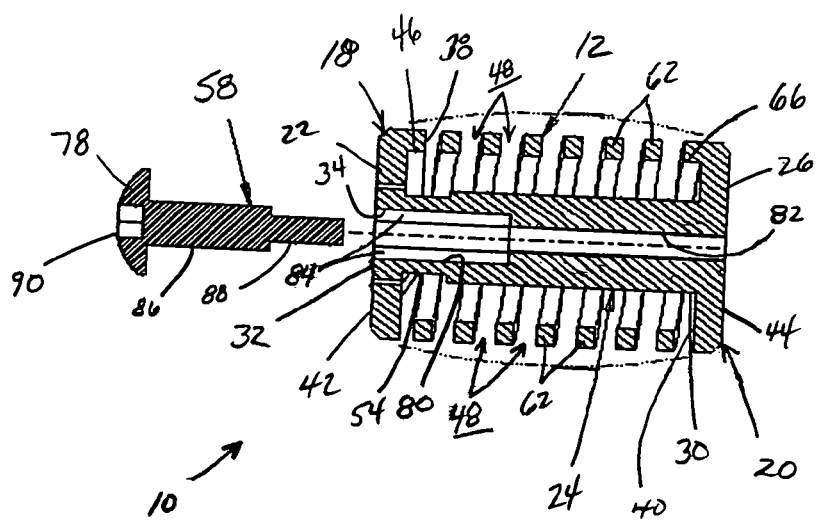
FIG. 7 is a cross-sectional view of the implant of FIG. 6, taken along line 7-7.

Referring now to FIG. 7, the first securing piece 18 includes a first end cap structure 22. The first end cap structure 22 has an inner surface 38 and an outer surface 42. Retaining structure 46 is formed on the inner surface 38 of the first end cap structure 22. Likewise, the second securing piece 20 includes a second end cap structure 26. The second end cap structure has an inner surface 40 and an outer surface 44. Retaining structure 66 is also formed on the inner surface 40 of the second end cap structure 26. In the illustrated embodiment, the retaining structures 46, 66 of each of the first and second end cap structures 22, 26 is a partial wall that projects axially outward from the inner surfaces 38, 40 along a portion of the perimeter of the first and second end cap structures 22, 26.

Figure 5:
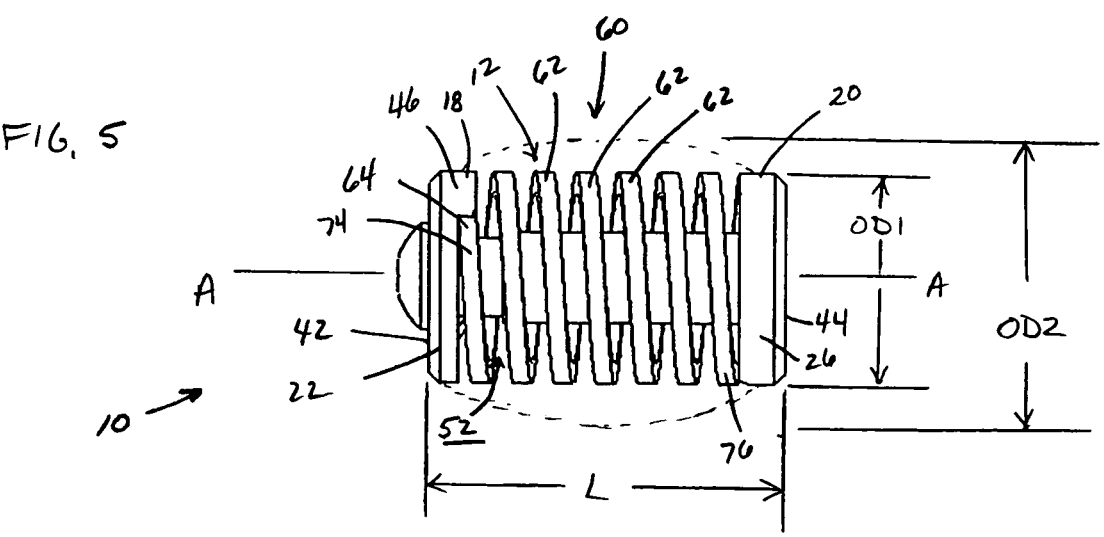
FIG. 5 is a side elevational view of the implant of FIG. 3.

Referring to FIG. 5, the helical body 12 includes a number of coils 62, including first and second end coils 74, 76. An end 64 (only one shown) of each of the end coils 74, 76 of the helical body 12 is permanently affixed to the retaining structures 46, 66. The ends 64 of the helical body 12 may be permanently affixed by welding or bonding the ends 64 to the retaining structures 46, 66. The end coils 74, 76 may also be affixed to the inner surfaces 38, 40 of each of the first and second end cap structures 22, 26. In some embodiments, the ends 64 of each of the end coils 74, 76 have a flattened surface (not shown) that abuts the inner surfaces 38, 40 and is secured (e.g. by welding or bonding) to the end cap structures 22, 26. Alternatively, the helical body 12 may be otherwise permanently affixed or attached or temporarily affixed or attached to the first and second end cap structures 22, 26 in accord with the principles disclosed.

Referring again to FIG. 7, the second end cap structure 26 is interconnected to a shaft 24. The shaft 24 extends axially outward from the inner surface 40 of the second end cap structure 26. The shaft has a first end 30 and a second end 32 that generally defines a longitudinal axis A-A of the implant 10 (FIG. 5). The coils 62 of the helical body 12 turn about the shaft 24 along the longitudinal axis A-A of the implant 10. The first end 30 of the shaft 24 is joined to the inner surface 40 of the second end cap structure 26. The shaft 24 and second end cap structure 26 may be integrally formed or fastened together to form the overall second securing piece 20.

Still referring to FIG. 7, a bore 34 extends at least partially through the shaft 24. The bore 34 includes a first region 80 and a second region 82. In the illustrated embodiment, the first region 80 of the bore 34 includes flats 84 (see also FIG. 6). The flats 84 are configured for receipt of a tool (not shown), as will be described in greater detail hereinafter. The second region 82 of the bore 34 is threaded. In the illustrated embodiment, the threaded second region 82 extends through the second securing piece 20 to ease manufacture of the threaded second region 82.

Figure 6:
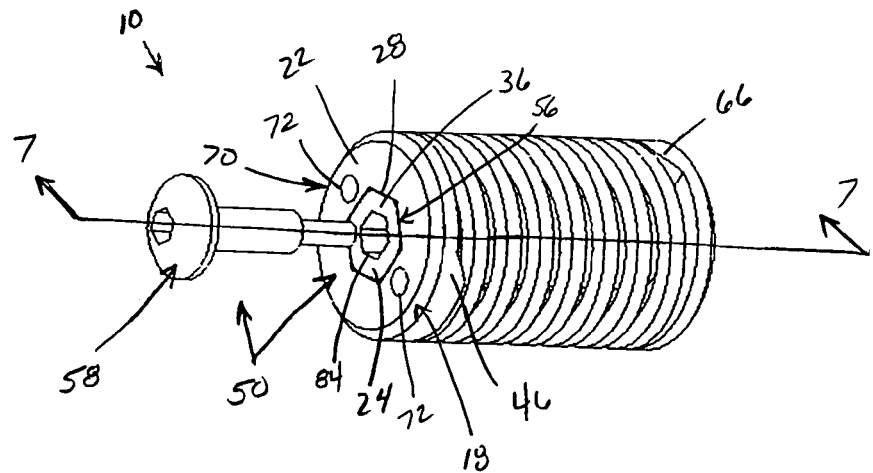
FIG. 6 is a front perspective view of the implant of FIG. 3, showing one embodiment of a locking arrangement of the implant, according to the principles of the present disclosure.

Referring now to FIG. 6, the second end 32 of the shaft 24 of the second securing piece 20 includes shaped structure 36 (FIG. 6). The first securing piece 20 includes interlock structure 28 (FIG. 6) that corresponds to the shaped structure 36 of the shaft 24. The shaped structure 26 and the interlock structure 28 prevent the first and second securing pieces 18, 20 from rotating relative to one another. In the illustrated embodiment, the interlock structure 28 includes an aperture 56 formed in the first end cap structure 22. The aperture 56 corresponds to the shaped structure 36 of the shaft 24.

The interlock structure 28 (i.e. the aperture 56) and the shaped structure 36 of the shaft 24 define the locking arrangement 50 of the implant. In particular, the shaped structure 26 of the shaft 24 mates with the interlock structure 28 of the first end cap structure 22 to prevent the first and second securing pieces 18, 20 from rotating or turning relative to one another. In the illustrated embodiment, the shaped structure 36 of the shaft 24 is a hex-shaped construction that corresponds to a hex-shape construction of the interlock structure 28. When mated or coupled, the first and second securing pieces 18, 20 are in a fixed relation to one another. In alternative embodiments, the interlock structure 28 can include other differently shaped mating structures that prevent the first and second securing pieces from rotating relative to one another.

In the illustrated embodiment, the locking arrangement 50 also includes a fastener 58, such as a setscrew, configured to secure the first and second securing pieces 18, 20 in a relative axial position. The setscrew 58 has a first guiding portion 86 and a second threaded portion 88. The guiding portion 86 is sized to fit within the first region of the bore 34 and guide the setscrew 58 during assembly or use. That is, the diameter of the guiding portion 86 fits within the flats 84 of the first region 80 to coaxially align the setscrew 58 with the shaft 24. The second threaded portion 88 of the setscrew is configured to engage the second threaded region 82 of the bore 34.

As shown in FIG. 7, when the second threaded portion 88 of the setscrew 58 is engaged with the second threaded region 82 of the shaft 24, a head 78 of the setscrew abuts or seats against the outer surface 42 of the first securing piece 18. The head 78 maintains the relative axial position of the first and second securing pieces 18, 20. A socket 90 is formed in the head 78 of the setscrew 58. The socket 90 is configured to receive of a tool, such as an allen wrench, for threading and un-threading the setscrew, as will be discussed hereinafter.

Referring again to FIG. 5, when assembled and in a relaxed configuration, the intervertebral implant 10 generally has an axial length L and a first outer diameter OD1. The length L of the implant 10 extends from the outer surface 42 of the first securing piece 18 to the outer surface 44 of the second securing piece 20. The length L of the external member is preferably between 0.5 and 1.2 inches; more preferably the length L is between 0.7 and 0.9 inches; and most preferably the length L is about 0.8 inches. The length of the intervertebral implant 10 generally corresponds to the size of a patient's spinal anatomy.

In the illustrated embodiment, the length L of the implant 10 is the same in both the non-expanded configuration and the expanded configuration. In alternative embodiments, it is contemplated that the axial length L of the implant can be adjustable. For example, the axial positioning of the first securing member 18 can be selectively positionable relative to the second securing member 20 by lengthening or shortening a setscrew configuration, or by varying the engagement depth of a setscrew.

The outer diameter OD of the implant is configured to expand (or contract from an expanded configuration) depending upon the direction of rotation of the first securing piece 18 relative to the second securing piece 20. That is, with the end coils 74, 76 of the helical body 12 permanently affixed to the first and second securing pieces 18, 20, rotation of one securing piece relative to the other causes the coils of the helical body to "wind" or "unwind."

In a relaxed or non-expanded configuration, the outer diameter OD1 of the implant 10 is typically between 6 and 20 mm. The size depends upon the particular needs of the patient and the application, that is, the desired distraction height between the two vertebral elements V1, V2. In an expanded configuration, the outer diameter OD2 expands by rotation of the helical body 12 in a direction that unwinds the helical body 12. In the expanded configuration, the outer diameter OD2 of the implant is preferably between 1 and 5 mm greater than the outer diameter OD1 of the implant in the non-expanded configuration. Accordingly, the two vertebral elements V1, V2 may be spatially separated, in the direction of expansion represented by arrow A in FIG. 2, a distance generally equivalent to between 1 and 5 mm.

Each of the outer diameters OD1, OD2 in the non-expanded and expanded configuration is generally defined as the outer diameter at a central region 60 of the implant. As can be understood, the outer diameter OD2 may, in some expanded configurations, be reduced at the first and second ends 14, 16 of the helical body 12, in comparison to the central region 60, as the ends 14, 16 are permanently affixed to the caps.

Referring back to FIG. 7, the helical body 12 of the expandable implant 10 defines open regions 48 between the coils 62 of the helical body 12. The open regions 48 encourage bone growth through the implant, and accordingly between the vertebral elements V1, V2 (FIGS. 1 and 2). In particular, the opening regions 48 provide access to the interior area 52 (FIG. 5) of the implant 10. When the implant 10 has been inserted and expanded between two vertebral elements V1, V2 (FIG. 2), bone growth material can be packed within the interior area of the implant through the open regions 48.

It is contemplated that a particular open region arrangement can be configured for use in a particular application by providing helical bodies having different coil configurations. For example, the helical body 12 may include coils 62 having different cross-sectional shapes, such as a circular, square, or rectangular shape. In addition, the coils may be more compactly designed, i.e. includes more coils per length L, or more openly designed, i.e. includes less coils per length L. In the illustrated embodiment, the implant 10 has between 5 and 8 coils per inch of length L.

As shown in FIG. 6, the implant 10 includes an implant handling arrangement 70. The implant handling arrangement 70 is configured so that the implant 10 can be handled and manipulated by a surgical tool (not shown) during a surgical procedure. The implant handling arrangement 70 of the illustrated embodiment is formed in the first end cap structure 22 of the first securing piece 18. The handling arrangement 70 includes first and second holes 72 sized to receive a distal end of the surgical tool.

In use, the intervertebral implant 10 is used to space and separate two vertebral elements V1, V2. The implantation procedure generally includes first selecting an implant 10 having the desired size and configuration. The selected implant is then grasped with the surgical tool via the implant handling arrangement 70. At this point in the procedure, the helical body 12 of the selected implant 10 is in the relaxed or non-expanded configuration.

The implant 10 is inserted between the two vertebral elements V1, V2 in the relaxed configuration, as shown in FIG. 1. The surgical tool is removed from the handling arrangement 70, and the setscrew 58 is removed from the shaft 24, for example, by applying an alien wrench to the socket 90 of the setscrew 58. The user then inserts another tool (e.g. a second allen wrench) into the first region 80 of the bore 34 of the shaft 24. The flats 84 of the first region 80 engage the wrench so that the second securing piece 20 can be held in a stationary position and prevented from rotating.

The surgical tool is then re-attached to the handling arrangement 70 of the first securing piece 18 by inserting the tool into the holes 72 of the handling arrangement 70. The helical body 12 preferably has a number of coils 62 configured such that the first securing piece 18 may be axially pushed toward the second securing piece 20 by the surgical tool. While the user is pushing the first securing piece 18 and compressing the helical body 12, the user also maintains the second securing piece 20 in the stationary position with the wrench, which is engaged with the flats 84 of the shaft 24.

Figure 8:
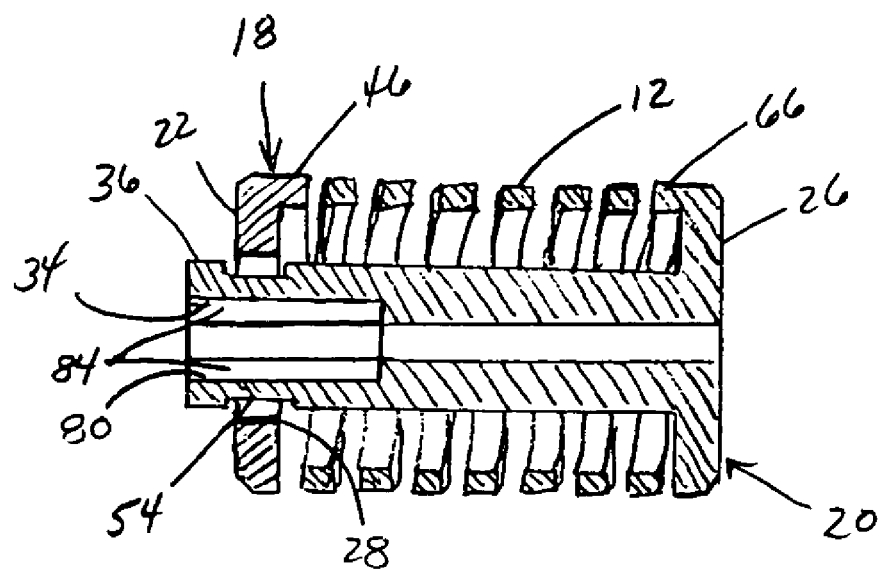
FIG. 8 is another cross-sectional view of the implant of FIG. 7.

As shown in FIGS. 7 and 8, the shaft 24 includes an annular recess 54. The annular recess 54 provides clearance such that the interlocking structure 28 of the first end cap structure 22 disengages from the shaped structure 36 of the shaft 24 when the interlocking structure 28 is pushed toward the second end cap structure 26 and positioned about the annular recess 54 of the shaft 24. In an alternative embodiment, the first securing piece 18 may be axially pulled in a direction away from the second securing piece 20 such that the interlock structure 28 of the first end cap structure 22 disengages from the shaped structure 36 of the shaft 24.

When the interlock structure 28 of the first securing piece 18 is disengaged from the shaped structure 36 of the shaft, the first securing piece 18 can then be rotated (un-wound), by the surgical tool, relative to the stationary second securing piece 20 to expand the outer diameter of the helical body 12. In particular, the first securing piece 18 can be angularly rotated, or un-wound, relative to the second securing piece 20, to a selected one of a plurality of rotational orientations. In the illustrated embodiment, each of the rotational orientations is incremental in that the degree of rotation is determined by the shaped structure 36 of the shaft 24 and interlock structure 28 of the first securing piece 18.

For example, the hex-shape of the shaped structure 36 and interlock structure 28 permit the securing pieces 18, 20 to rotate and lock at 60-degree increments relative to one another. Other shaft 24 and interlock structure 28 configurations can be used to provide different increments of angular rotation. It is to be understood, that depending upon the helical body configuration, the securing pieces 18, 20 may be configured to rotate relative to one another to a maximum angular position that is less than, equal to, or greater than 360 degrees from an initial angular position defined by the relaxed configuration.

When the desired expanded configuration of the implant 10 is achieved by rotation of the first securing piece 18 relative to the second securing piece 20, the interlock structure 28 is re-engaged with the shaped structure 36 of the shaft 24 to lock the relative positions of the first and second securing pieces 18, 20. The setscrew 58 is then reengaged with the shaft 24 to axially secure the implant in the expanded configuration.

As can be understood, the implant 10 may be contracted from an expanded configuration to a reduced dimension or a non-expanded configuration. This arrangement permits a user to adjust (i.e. expand or contract) the outer dimension of the implant 10 a number of times, as needed, during a surgical procedure. Likewise, the implant 10 may also be contracted for removal after installation and expansion.

Referring now to FIGS. 9-11, a second embodiment of an expandable intervertebral implant 210 is illustrated. Similar to the previous embodiment, the implant 210 generally includes a helical body 212 having a first end 214 and a second end 216. The first end 214 of the helical body 212 is attached to a first securing piece 218, and the second end 216 is attached to a second securing piece 220.

The implant 210 may be introduced into an implant site in a compact or compressed configuration as shown in FIG. 10 (i.e. wound down to reduce an outer diameter of the helical body 212). The compact configuration of the implant 210 reduces the area and volume required for insertion, which further minimizes the invasiveness of an implant procedure. Once inserted, the compressed implant 210 may be released or expanded to an expanded configuration as shown in FIG. 11 to achieve the desired distraction.

As shown in FIGS. 10 and 11, the intervertebral implant 210 is configured to expand from a first dimension to a selected second dimension. Similar to the previous embodiment, the implant 210 includes a locking arrangement 250 that secures the implant at the selected second dimension. That is, the implant 210 is configured to permit expansion to, and be secured at, a selected one of a variety of second dimensions.

Expansion is accomplished by permitting rotation of one end 214, 216 of the helical body 212 in relation to the other end 214, 216.

The first securing piece 218 includes a first end cap structure 222 having a first exterior surface 243 (FIG. 10). The second securing piece 220 includes a second end cap structure 226 having a second exterior surface 245 (FIG. 11). The helical body 212 includes a number of coils 262, including first and second end coils 274, 276. Each of the end coils 274, 276 of the helical body 212 is permanently affixed to the first and second exterior surfaces 243, 245 of the first and second end cap structures 222, 226.

The end coils 274, 276 of the helical body 212 may be permanently affixed by welding or bonding the end coils to the exterior surfaces 243, 245.

The second end cap structure 226 is interconnected to a shaft 224. The shaft 224 extends axially outward from the second end cap structure 226. The shaft generally defines a longitudinal axis A'-A' of the implant 210 (FIG. 9). The coils 262 of the helical body 212 turn about the shaft 224 along the longitudinal axis A-A of the implant 210.

An interlock structure (shown with respect to the first embodiment and referenced as number 28 in FIG. 6) formed in the first end cap 218 and the shaft 224 define the locking arrangement 250 of the implant 210. As previously described, the shaft 224 mates with the interlock structure of the first end cap structure 222 to prevent the first and second securing pieces 218, 220 from rotating or turning relative to one another. The locking arrangement 250 may also includes a fastener or setscrew (shown in the first embodiment, FIG. 6) to secure the first and second securing pieces 218, 220 in a relative axial position.

The outer diameter of the implant 210 is configured to expand or contract depending upon the direction of rotation of the first securing piece 218 relative to the second securing piece 220. That is, with the end coils 274, 276 of the helical body 212 permanently affixed to the first and second securing pieces 218, 220, rotation of one securing piece relative to the other causes the coils of the helical body to "wind" or "unwind."

FIG. 10 illustrates the second embodiment of the implant 210 in the compact or non-expanded configuration, i.e. the coils have been wound down to reduce the outer diameter of the helical body 212. In this configuration, the intervertebral implant 210 has a first outer diameter OD1'. The compact configuration of the implant 210 reduces the area and volume required for insertion at an implant site.

Once inserted, the non-expanded implant 210 may be released to expand. When released, the helical body 212 unwinds to a relaxed or expanded configuration, as shown in FIG. 11. In the expanded configuration, the intervertebral implant 210 has a second outer diameter OD2' that is greater the first outer diameter OD1'.

It is contemplated that in addition to permitting the implant 210 to expand from the compressed configuration to the relaxed or first expanded configuration, as shown in FIG. 11, the helical coil 212 of the implant 210 may further be un-wound (as described with regards to the first embodiment) to further expand the helical body 212 to yet a larger, second expanded configuration.

In each of the first and second embodiment, the implants 10, 210 are positionable in the non-expanded orientation and the expanded orientation; yet, the helical bodies 12, 212 of the implants are in different states for each orientation. Specifically, in the non-expanded orientation, the first implant embodiment 10 is in a relaxed state, and the second implant embodiment 210 is in a wound or compact state. In the expanded configuration, the first implant embodiment 10 is in an un-wound state, and the second implant embodiment 210 is in a relaxed state. In either embodiment, rotation of the first securing piece 18, 218 relative to the second securing piece 20, 220 selectively adjusts the outer dimension of the implant 10, 210 to provide a desired distraction height.

The above specification provides a complete description of the EXPANDABLE HELICAL IMPLANT. Since many embodiments of the invention can be made without departing from the spirit and scope of the invention, the invention resides in the claims hereinafter appended.

What is claimed is:

1. An expandable intervertebral implant, comprising:
a) a first securing piece and a second securing piece, the first securing piece forming a first end of the implant and the second securing piece forming a second end of the implant;
b) a helical body having a first end and a second end, the first end of the helical body being rotatable relative to the second end of the helical body, the first end of the helical body being permanently affixed to the first securing piece and the second end of the helical body being permanently affixed to the second securing piece; and
c) a locking arrangement extending through the helical body and operatively connecting the first and second securing pieces together, the locking arrangement being configured to selectively lock the second securing piece in a rotational orientation relative to the first securing piece;
wherein the helical body is configured to radially expand from a non-expanded configuration to an expanded configuration by rotating the first securing piece relative to the second securing piece in a direction to unwind the helical body.

2. The implant of claim 1 wherein the helical body is in a relaxed state when in the non-expanded configuration.

3. The implant of claim 1 wherein the helical body is in a wound state when in the non-expanded configuration.

4. The implant of claim 1 wherein a length of the implant remains the same when in the non-expanded configuration and when in the expanded configuration.

5. The implant claim 1, wherein the locking arrangement is configured to lock the second piece relative to the first piece in one of a plurality of rotational orientations.

6. The implant of claim 5, wherein each of the plurality of rotational orientations corresponds to one of a plurality of expanded configurations, each of the expanded configurations having a different expansion dimension.

7. The implant of claim 1, wherein the locking arrangement includes a shaft interconnected to the second securing piece and a corresponding aperture formed in the first securing piece, the shaft and aperture being configured to engage and lock the second securing piece in the rotational orientation relative to the first securing piece.

8. The implant of claim 7, wherein the shaft is hex-shaped and configured to lock the second securing piece relative to the first securing piece in one of a plurality of incremental rotational orientations.

9. The implant of claim 7, wherein the locking arrangement further includes a fastener configured to axially secure the second securing device relative to the first securing device.

10. The implant of claim 1, wherein the first securing piece includes a handling arrangement for handling the implant during a surgical procedure.

11. A method of expanding an expandable intervertebral implant, the method comprising the steps of:
a) providing an implant having a helical body permanently affixed to a first end cap and a second end cap, the first and second end caps being substantially at a first and second end of the implant and being operatively connected together by a locking arrangement extending through the helical body;
b) inserting the implant at an implant site;
c) radially expanding the implant by rotating the first end cap relative to the second end cap so that a first end of the helical body rotates relative to a second end of the helical body such that the helical body radially expands from a first configuration to a second configuration; and
d) locking the implant in the second configuration with the locking arrangement.

12. The method of claim 11, wherein the step of rotating the first end cap relative to the second end cap includes unwinding the helical body of the implant to radially expand the helical body from the first configuration to the second configuration.

13. The method of claim 12, wherein the step of unwinding the helical body of the implant includes unwinding the body from the first configuration, wherein the body is in a relaxed state, to the second configuration.

14. The method of claim 12, wherein the step of unwinding the helical body of the implant includes unwinding the body from the first configuration, wherein the body is in a wound state, to the second configuration.

15. The method of claim 12, wherein the step of expanding the implant includes disengaging the locking arrangement of the implant such that the first end cap is free to rotate relative to the second end cap.

16. The method of claim 15, further including maintaining the rotational position of the second end cap while rotating the first end cap.

17. The method of claim 15, wherein the step of locking the implant in the second configuration includes engaging the locking arrangement of the implant such that the first end cap is rotationally fixed relative to the second end cap.

18. The method of claim 17, wherein the step of locking the implant further includes locking the first end cap in an axially position relative to the second end cap.

19. The method of claim 11, wherein the step of expanding the implant includes incrementally expanding the implant by rotating the first end cap to one of a plurality of rotational orientations.

* * * * *

UNITED STATES PATENT AND TRADEMARK OFFICE
CERTIFICATE OF CORRECTION

PATENT NO.        : 7,297,162 B2
APPLICATION NO. : 10/865673
DATED             : November 20, 2007
INVENTOR(S)       : James R. Mujwid It is certified that error appears in the above-identified patent and that said Letters Patent is hereby corrected as shown below:

In column 2, line 12, change "FIG. 3 is front perspective view" to --FIG. 3 is a front perspective view--.

In column 3, lines 27-28, change "is a partial wall that projects axially outward" to --are partial walls that project axially outward--.

In column 4, line 22, change "corresponds to a hex-shape construction" to --corresponds to a hex-shaped construction--.

In column 4, line 48, change "configured to receive of a tool," to --configured to receive a tool,--.

In column 4, line 58, change "is between 0.7 and 0.9 inches;" to --is between 0.7 and 0.9 inch;--.

In column 4, line 59, change "is about 0.8 inches." to --is about 0.8 inch.--.

In column 5, line 27, change "expanded configuration is generally" to --expanded configurations is generally--.

In column 6, line 9, change "by applying an alien wrench" to --by applying an allen wrench--.

In column 7, line 60, change "may also includes" to --may also include--.

In column 8, line 25, change "first and second embodiment," to --first and second embodiments,--.

UNITED STATES PATENT AND TRADEMARK OFFICE
CERTIFICATE OF CORRECTION

PATENT NO. : 7,297,162 B2
APPLICATION NO. : 10/865673
DATED : November 20, 2007
INVENTOR(S) : James R. Mujwid It is certified that error appears in the above-identified patent and that said Letters Patent is hereby corrected as shown below:

In claim 5, column 9, line 8 change "The implant claim 1," to --The implant of claim 1,--.

In claim 18, column 10, lines 33-34 change "the first end cap in an axially position" to --the first end cap in an axial position--.

Signed and Sealed this

Twenty-ninth Day of July, 2008

JON W. DUDAS
*Director of the United States Patent and Trademark Office*